United States Patent [19]

Siret et al.

[11] Patent Number: 5,008,259
[45] Date of Patent: Apr. 16, 1991

[54] CEPHALOSPORIN COMPOUNDS

[75] Inventors: Patrice J. Siret, Reims; Frederick H. Jung, Rilly la Montagne, both of France; William Bell, Macclesfield, England

[73] Assignees: Imperial Chemical Industries PLC, London, England; I.C.I.-PHARMA, Gergy Cedex, France

[21] Appl. No.: 349,663

[22] Filed: May 10, 1989

[30] Foreign Application Priority Data

May 10, 1988 [GB] United Kingdom ............... 88401143

[51] Int. Cl.$^5$ ................. C07D 501/38; A61K 31/545
[52] U.S. Cl. ..................................... 514/202; 540/222
[58] Field of Search ................ 540/221, 222; 514/202, 514/206

[56] References Cited

U.S. PATENT DOCUMENTS 4,855,420  8/1989  Jung ..................................... 540/222

FOREIGN PATENT DOCUMENTS 0267733  5/1988  European Pat. Off. .

Primary Examiner—Nicholas S. Rizzo
Attorney, Agent, or Firm—Cushman, Darby & Cushman

[57] ABSTRACT

Cephalosporin antibiotics having a 3-position substituent of the formula:

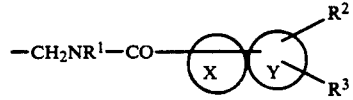

are described, wherein $R^1$ is hydrogen or certain optionally substituted alkyl groups; X is a benzene ring or certain 5 or 6-membered heterocyclic ring and is fused to ring Y which is a nitrogen containing heteroaryl group; $R^2$ and $R^3$ are independently hydroxy or an in vivo hydrolysable ester thereof, and ring system X-Y is optionally substituted. Processes for their preparation and use are described.

8 Claims, No Drawings

CEPHALOSPORIN COMPOUNDS

The present invention relates to cephalosporins and in particular to such compounds comprising an amide group. This invention further relates to processes for their preparation, to intermediates in their preparation, to their use as therapeutic agents and to pharmaceutical compositions containing them. The compounds of this invention are antibiotics and can be used in the treatment of any disease that is conventionally treated with antibiotics for example in the treatment of bacterial infection in mammals including humans. The compounds of this invention also have non-therapeutic uses as they can be used in conventional manner in industry for example they can be used as disinfectants and food preservatives. The compounds of this invention, however, are primarily of therapeutic interest as they show a desirable profile of activity and duration in their antibacterial effect.

Investigation into new cephalosporin derivatives has been intense over the past 25 years with many thousands of patents and scientific papers having been published. A particular problem associated with the commercially available cephalosporins is the lack of potency against strains of Pseudomonas. The present invention provides cephalosporin derivatives having novel 3-position substituents, which derivatives possess good antibacterial activity and in particular against strains of Pseudomonas.

A further problem associated with many commercially available cephalosporins is the lack of stability to β-lactamase enzyme producing organisms and the consequent loss of antibacterial activity. The compounds of the present invention exhibit good stability to β-lactamase enzymes and thus are particularly useful in treating organisms that are β-lactamase producers.

The cephalosporin derivatives referred to herein are generally named in accordance with the 'cephem' nomenclature and numbering system proposed in J.A.C.S. 1962, 84,3400 and as depicted hereinbelow:

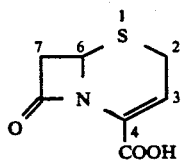

Accordingly the present invention provides a cephalosporin compound having a 3-position substituent of the formula (I):

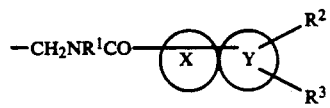

wherein:

$R^1$ is hydrogen, $C_{1-6}$alkyl optionally substituted by halo, hydroxy, $C_{1-4}$alkoxy, carboxy, amino, cyano, $C_{1-6}$alkanoylamino, phenyl or heteroaryl, or $R^1$ is $C_{2-6}$alkenyl;

X is a 5- or 6-membered ring selected from a group of the sub-formulae (a)-(b):

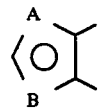

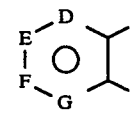

wherein A is CH or a nitrogen atom; B is oxygen, sulphur or a group $NR^4$; zero, one or two of D, E, F and G are nitrogen atoms and the remainder are CH groups: or X is a pyrazinone, pyridinone, pyridazinone or pyrimidinone ring, or is a thione equivalent of such a ring, said rings having a substituent $R^4$ on one nitrogen atom, or is pyranone, or pyranthione; the ring X being fused by any two adjacent carbon atoms to ring Y;

ring Y is a 6-membered heteroaryl ring containing one or two ring nitrogen atoms, substituted on adjacent carbon atoms by groups $R^2$ and $R^3$;

wherein either ring of the fused X-Y ring system is bonded via a carbon atom to the amide linkage;

$R^2$ is hydroxy or an in vivo hydrolysable ester thereof;

$R^3$ is ortho to $R^2$ is hydroxy or an in vivo hydrolysable ester thereof;

$R^4$ is hydrogen, hydroxy, $C_{1-6}$alkoxy, phenoxy, $C_{2-6}$alkenyl or $C_{1-6}$alkyl, (any of these groups being optionally substituted by hydroxy, $C_{1-6}$alkoxy, cyano, amino, $C_{1-6}$alkylamino, di-$C_{1-6}$alkylamino, carboxy, $C_{1-6}$alkoxycarbonyl, $C_{1-6}$alkanoyloxy, carbamoyl, $C_{1-6}$alkylcarbamoyl, di-$C_{1-6}$alkylcarbamoyl, $C_{1-6}$alkoxycarbonylamino, phenyl, phenyl$C_{1-6}$alkyl, carboxyaminocarbonyl, $C_{1-6}$alkoxycarbonylaminocarbonyl, benzoyl or $C_{3-8}$cycloalkyl) or $R^4$ is phenyl, $C_{3-8}$cycloalkyl, amino, $C_{1-6}$alkylamino or di-$C_{1-6}$alkylamino:

wherein the fused X-Y ring system and/or any phenyl group is optionally substituted by $C_{1-6}$alkyl, halo, hydroxy, hydroxy $C_{1-6}$alkyl, cyano, trifluoromethyl, nitro, amino, $C_{1-6}$alkylamino, di-$C_{1-6}$alkylamino, $C_{1-6}$alkanoyl, $C_{1-6}$alkoxy, $C_{1-6}$alkylthio, $C_{1-6}$alkanoyloxy, carbamoyl, $C_{1-6}$alkylcarbamoyl, di-$C_{1-6}$alkyl carbamoyl, carboxy, carboxy $C_{1-6}$alkyl, $C_{1-6}$alkoxycarbonyl$C_{1-6}$alkyl, sulpho, sulpho$C_{1-6}$alkyl, sulphonamido $C_{1-6}$alkyl, $C_{1-6}$alkoxycarbonyl, $C_{1-6}$alkanoylamino, thioureido or amidino.

In one aspect $R^1$ may be $C_{1-6}$alkyl substituted by heteroaryl. Suitably such a heteroaryl group is a 5- or 6-membered ring containing 1, 2 or 3 heteroatoms selected from nitrogen, oxygen and sulphur and may be optionally substituted, for example by the substituents described hereinbefore with respect to the fused X-Y ring system. For example $R^1$ may be pyridinylmethyl or furanylmethyl.

Particular meanings for $R^1$ are hydrogen, $C_{1-6}$alkyl for example methyl, ethyl or propyl, hydroxy $C_{1-6}$alkyl for example 2-hydroxyethyl, halo $C_{1-6}$alkyl for example 2-chloroethyl or 2-fluoroethyl, $C_{1-6}$alkoxy $C_{1-6}$alkyl for example 2-methoxyethyl, 2-ethoxyethyl or methoxymethyl, carboxy $C_{1-6}$alkyl for example carboxymethyl, phenyl $C_{1-6}$alkyl for example benzyl or phenethyl, or $C_{2-6}$alkenyl for example allyl.

Preferably R¹ is hydrogen, methyl or ethyl. Most preferably R¹ is hydrogen.

In one aspect X is a ring of the sub-formula (a) as hereinbefore described, that is X is an imidazole, thiazole, oxazole, pyrrole, furan or thiophen ring.

In another aspect X is a ring of the sub-formula (b) as hereinbefore described, for example benzene, pyridine, pyrimidine, pyrazine or pyridazine.

In a further aspect X is a pyrazinone, pyridinone, pyridazinone or pyrimidinone ring, or the thione equivalent of such rings, said rings having a substituent R⁴ on one nitrogen atom. Y is a 6-membered heteroaryl ring containing either one or two ring nitrogen atoms; for example Y is pyridine, pyrimidine, pyrazine or pyridazine. For example the X-Y fused ring system may be of the sub-formula (i)-(x):

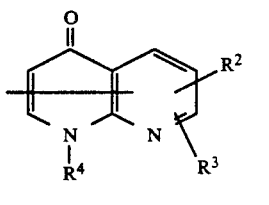 (i)

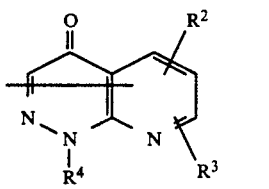 (ii)

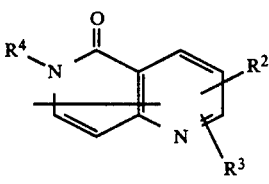 (iii)

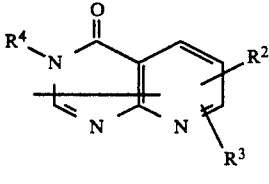 (iv)

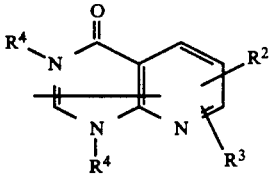 (v)

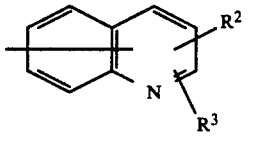 (viii)

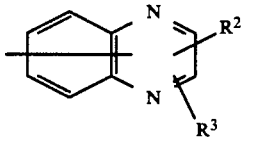 (vii)

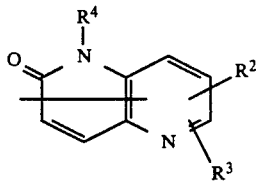 (vi)

-continued

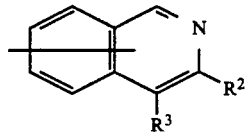 (ix)

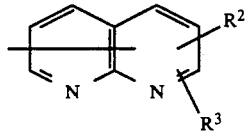 (x)

Particular meanings of the group R⁴ are hydrogen, $C_{1-6}$alkoxy for example methoxy or ethoxy, $C_{1-6}$alkyl for example methyl, ethyl, n-propyl, isopropyl, n-butyl or isobutyl, $C_{3-8}$cycloalkyl for example cyclopropyl, hydroxy $C_{1-6}$alkyl for example hydroxymethyl or hydroxyethyl, phenyl or phenyl$C_{1-6}$alkyl for example benzyl or phenethyl. Preferably R⁴ is hydrogen, methoxy, ethoxy, methyl, ethyl or benzyl.

Preferred values for the X-Y fused ring system are those of the sub-formulae (i) and (v).

In another preferred aspect the X ring is a pyran-4-one ring. In alternative the X ring is a pyran-4-thione ring.

R² is hydroxy or an in vivo hydrolysable ester thereof. In vivo hydrolysable esters are those pharmaceutically acceptable esters that hydrolyse in the human or animal body to produce the parent hydroxy compound. Such esters can be identified by administering, e.g. intravenously to a test animal, the compound under test and subsequently examining the test animal's body fluids. Suitable in vivo hydrolysable esters include $C_{1-6}$alkanoyloxy for example acetoxy, propionyloxy, pivaloyloxy, $C_{1-4}$alkoxycarbonyloxy for example ethoxycarbonyloxy, phenylacetoxy and phthalidyl.

R³ is hydroxy or an in vivo hydrolysable ester thereof.

Conveniently both R² and R³ have the same value and are both hydroxy or are both in vivo hydrolysable esters, for example they are both acetoxy or pivaloyloxy.

For the avoidance of doubt, the amide group (—CH₂NR¹CO—) can be linked to either ring X or ring Y of the fused X-Y ring system. Substituents R² and R³ are located on ring Y.

As stated hereinbefore the fused X-Y ring system may be optionally substituted on either ring. Particular substituents are $C_{1-6}$alkyl for example methyl or ethyl, halo for example chloro, fluoro or bromo, hydroxy, hydroxy$C_{1-6}$alkyl for example hydroxyethyl, amino, $C_{1-6}$alkylamino for example methylamino or ethylamino, di-$C_{1-6}$alkyl amino for example dimethylamino or diethylamino, $C_{1-6}$alkoxy for example methoxy or ethoxy, carboxy $C_{1-6}$alkyl for example carboxymethyl, $C_{1-6}$alkanoylamino for example acetamido, trifluoromethyl, carboxy, carbamoyl, $C_{1-6}$alkylcarbamoyl for example methylcarbamoyl, di-$C_{1-6}$alkylcarbamoyl for example dimethylcarbamoyl, $C_{1-6}$alkanoyl for example acetyl and $C_{1-6}$alkylthio for example methylthio.

A favoured class of cephalosporin compounds of the present invention has a 3-position substituent of the formula (II):

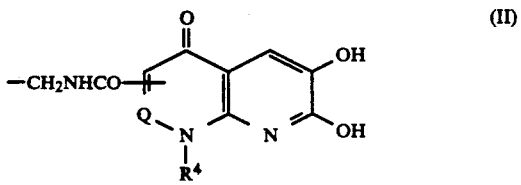

wherein Q is CH or N and $R^4$ is hydrogen, $C_{1-6}$alkyl or $C_{1-6}$alkoxy.

Another favoured class of cephalosporin compounds of the present invention has a 3-position substituent of the formula (III):

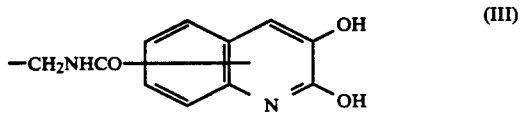

As stated hereinbefore the present invention relates to cephalosporins having a novel 3-position substituent. A particular class of cephalosporins within the present invention is that of the formula IV:

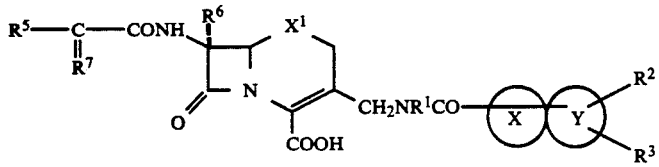

and salts and esters thereof wherein $R^1$-$R^3$, X and Y are as hereinbefore defined;

$X^1$ is sulphur, oxygen, methylene or sulphinyl;

$R^6$ is hydrogen, methoxy or formamido; and $R^5$ and $R^7$ are groups known for such positions in the cephalosporin art.

Preferably $X^1$ is sulphur.

Preferably $R^6$ is hydrogen.

$R^5$ is for example 2-aminothiazol-4-yl or 2-aminooxazol-4-yl each optionally substituted in the 5-position by fluorine, chlorine or bromine, or $R^5$ is 5-aminoisothiazol-3-yl, 5-amino-1,2,4-thiadiazol-3-yl, 3-aminopyrazol-5-yl, 3-aminopyrazol-4-yl, 2-aminopyrimidin-5-yl, 2-aminopyrid-6-yl, 4-aminopyrimidin-2-yl, 2-amino-1,3,4-thiadiazol-5-yl or 5-amino-1-methyl-1,2,4-triazol-3-yl;

$R^7$ is for example of the formula $=N.O.R^8$ (having the syn configuration about the double bond) wherein $R^8$ is hydrogen, (1-6C)alkyl, (3-8C)cycloalkyl, (1-3C)alkyl(3-6C)cycloalkyl, (3-6C)cycloalkyl(1-3C)alkyl, (3-6C)alkenyl, optionally substituted by carboxy, (5-8C)cycloalkenyl, (3-6C)alkynyl, (2-5C)alkylcarbamoyl, phenylcarbamoyl, benzylcarbamoyl, (1-4C)alkylcarbamoyl(1-4C)alkyl, di(1-4C)alkylcarbamoyl(1-4C)alkyl, (1-4C)haloalkylcarbamoyl(1-4C)alkyl, (1-3C)haloalkyl, (2-6C)hydroxyalkyl, (1-4C)alkoxy(2-4C)alkyl, (1-4C)alkylthio(2-4C)alkyl, (1-4C)alkanesulphinyl(1-4C)alkyl, (1-4C)alkanesulphonyl (1-4C)alkyl, (2-6C)aminoalkyl, (1-4C)alkylamino(1-6C)alkyl, (2-8C)dialkylamino(2-6C)alkyl, (1-5C)cyanoalkyl, 3-amino-3-carboxypropyl, 2-(amidinothio)ethyl, 2-(N-aminoamidinothio)ethyl, tetrahydropyran-2-yl, thietan-3yl, 2-oxopyrrolidinyl, or 2-oxotetrahydrofuranyl, or $R^8$ is of the formula V:

$$-(CH_2)_q-C(COOH)=CR^9R^{10} \qquad (V)$$

wherein q is one or two and $R^9$ and $R^{10}$ are independently hydrogen or $C_{1-4}$alkyl; or $R^8$ is of the formula VI:

$$-CR^{11}R^{12}-(CH_2)_r-COR^{13} \qquad VI$$

wherein r is 0-3, $R^{11}$ is hydrogen, (1-3C)alkyl or methylthio, $R^{12}$ is hydrogen, (1-3C)alkyl, (3-7C)cycloalkyl, cyano, carboxy, (2-5C)carboxyalkyl or methanesulphonylamino, or $R^{11}$ and $R^{12}$ are joined to form, together with the carbon to which they are attached, a (3-7C)carbocyclic ring, and $R^{13}$ is hydroxy, amino, (1-4C)alkoxy, (1-4C) alkylamino or of the formula $NHOR^{14}$ in which $R^{14}$ is hydrogen or (1-4C)alkyl;

or $R^7$ may be of the formula $=CH.R^{15}$ wherein $R^{15}$ is hydrogen, halogen, (1-6C)alkyl, (3-7C)cycloalkyl, (2-6C)alkenyl, (3-7C)cycloalkenyl, phenyl or benzyl.

Particular meanings for $R^8$ are hydrogen, methyl, ethyl, isopropyl, t-butyl, cyclopropyl, cyclobutyl, cyclopentyl, cyclohexyl, methylcyclopropyl, methylcyclobutyl, methylcyclopentyl, methylcyclohexyl, cyclopropylmethyl, cyclobutylmethyl, cyclopentylmethyl, allyl, cyclopentenyl, cyclohexenyl, propargyl, methylcarbamoyl, ethylcarbamoyl, phenylcarbamoyl, benzylcarbamoyl, 2-chloroethyl, 2-fluoroethyl, 2-bromoethyl, 2-hydroxyethyl, 3-hydroxypropyl, 2-methoxyethyl, 2-ethoxyethyl, 2-methylthio-ethyl, 2-methanesulphinylethyl, 2-methanesulphonyl-ethyl, 2-aminoethyl, 3-aminopropyl, 2-methylamino ethyl, 2-dimethylaminoethyl, cyanomethyl, 2-cyanoethyl, azidomethyl, 2-azidoethyl, ureidomethyl, 3-amino-3-carboxypropyl, 2-(amidino)ethyl, 2-(N-aminoamidino)-ethyl, tetrahydropyran-2-yl, thietan-3-yl, 2-oxopyrrolidinyl and 2-oxotetrahydrofuran-3-yl, or, when $R^8$ is of the formula V in which q is 1 or 2, a particular meaning for $R^8$ is when $R^9$ and $R^{10}$ are hydrogen and methyl, or, when $R^8$ is of the formula VI, a particular meaning for $R^8$ is when r=0 and $R^{11}$ is hydrogen, methyl or methylthio, $R^{12}$ is hydrogen, methyl, cyclopropyl, cyclobutyl, cyclopentyl, cyclohexyl, cyano, carboxy, carboxymethyl, 2-carboxyethyl or methanesulphonylamino, or when $R^{11}$ and $R^{12}$ are joined to form, together with the carbon to which they are attached, a cyclopropane, cyclobutane, cyclopentane, cyclohexane or cycloheptane ring and $R^{13}$ is hydroxy, amino, methoxy, ethoxy, methylamino, ethylamino, or of the formula $NHOR^{14}$ in which $R^{14}$ is hydrogen, methyl or ethyl.

Preferably $R^8$ is $C_{1-6}$alkyl for example methyl or ethyl, 1-carboxycyclobutyl, 1-carboxycyclopentyl, or 2-carboxyprop-2-yl. In particular $R^8$ is 2-carboxyprop-2-yl.

Particular meanings for $R^{15}$ are hydrogen, methyl, ethyl or chlorine.

The cephalosporin derivatives referred to herein are generally named in accordance with the 'cephem' nomenclature and numbering system proposed in J.A.C.S. 1962, 84,3400.

A particularly preferred class of cephalosporins of the present invention is that wherein $R^5$ is 2-aminothiazol-4-yl, $R^7$ is a group $=NOR^8$ wherein $R^8$ is $C_{1-6}$alkyl, 1-carboxycyclobutyl, 1-carboxycyclopentyl or 2-carboxyprop-2yl, $R^6$ is hydrogen, $X^1$ is sulphur and the 3-position substituent is of the formula (II) or (III).

It should be realised, of course, that the present invention covers all tautomeric forms, for example the sub-formulae (i)-(vi) are depicted in the keto form; where possible these may exist and be depicted in the enol form. Such tautomers are, of course, within the scope of the present invention. Furthermore, where possible, the X ring may be optionally substituted by hydroxy and this may exist in the tautomeric keto form. In addition the groups $R^2$ and $R^3$ may be hydroxy and may exist, where possible, in the tautomeric keto form.

As stated hereinbefore the compounds of this invention are primarily intended for use in therapy. Therefore in a preferred aspect the present invention provides a cephalosporin compound having a 3-position substituent of the formula I or a pharmaceutically acceptable salt or ester thereof. Suitable salts include acid addition salts such as hydrochloride, hydrobromide, citrate, maleate and salts formed with phosphoric and sulphuric acid. In another aspect suitable salts are base salts such as an alkali metal salt for example sodium or potassium, an alkaline earth metal salt for example calcium or magnesium, an organic amine salt for example triethylamine, morpholine, N-methylpiperidine, N-ethylpiperidine, procaine, dibenzylamine or N,N-dibenzylethylamine.

In order to use a compound of the present invention or a pharmaceutically acceptable salt or ester thereof for the therapeutic treatment of mammals including humans, in particular in treating infection, it is normally formulated in accordance with standard pharmaceutical practice as a pharmaceutical composition.

Therefore in another aspect the present invention provides a pharmaceutical composition which comprises a cephalosporin compound having a 3-position substituent of the formula I or a pharmaceutically acceptable salt or ester thereof and a pharmaceutically acceptable carrier.

The pharmaceutical composition of this invention may be administered in standard manner for the disease condition that it is desired to treat, for example by oral, rectal or parenteral administration. For these purposes it may be formulated by means known to the art into the form of, for example, tablets, capsules, aqueous or oily solutions or suspensions, emulsions, dispersible powders, suppositories and sterile injectable aqueous or oily solutions or suspensions.

In addition to the pharmaceutically acceptable cephalosporin derivative of the present invention the pharmaceutical composition of the invention may also contain, or be co-administered with, one or more known drugs selected from other clinically useful antibacterial agents (for example other beta-lactams or aminoglycosides), inhibitors of beta-lactamase (for example clavulanic acid), renal tubular blocking agents (e.g. probenicid) and inhibitors of metabolising enzymes (for example inhibitors of peptidases, for example Z-2-acylamino-3-substituted propenoates).

A preferred pharmaceutical composition of the invention is one suitable for intravenous, subcutaneous or intramuscular injection, for example a sterile injectable containing between 1 and 50% w/w of the cephalosporin derivative, or one suitable for oral administration in unit dosage form, for example a tablet or capsule which contains between 100 mg. and 1 g. of the cephalosporin derivative.

The pharmaceutical compositions of the invention will normally be administered to man in order to combat infections caused by bacteria, in the same general manner as that employed for cephalothin, cefoxitin, cephradine, ceftazidime and other known clinically used cephalosporin derivatives, due allowance being made in terms of dose levels for the potency of the cephalosporin derivative of the present invention relative to the known clinically used cephalosporins. Thus each patient will receive a daily intravenous, subcutaneous or intramuscular dose of 0.05 to 30 g., and preferably 0.1 to 10 g., of the cephalosporin derivative, the composition being administered 1 to 4 times per day, preferably 1 or 2 times a day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose. Thus a preferred daily oral dose is 0.5 to 10 g. of the cephalosporin derivative, the composition being administered 1 to 4 times per day.

In a further aspect the present invention provides a process for preparing a cephalosporin compound having a 3-position substituent of the formula I, which process comprises:

(a) reacting a cephalosporin compound having a 3-position substituent of the formula:

—$CH_2NHR^1$ wherein $R^1$ is as hereinbefore defined with a compound of the formula VII:

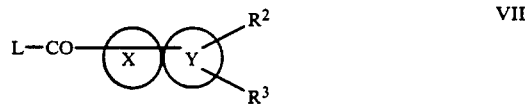

wherein X, Y, $R^2$ and $R^3$ are as hereinbefore defined and L is a leaving group; or (b) for compounds of the formula IV, reacting a compound of the formula VIII with a compound of the formula IX or a reactive derivative thereof:

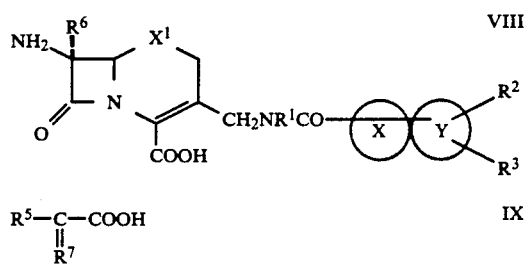

wherein $R^1$, $R^2$, $R^3$, $X^1$, X, Y, $R^5$, $R^6$ and $R^7$ are as hereinbefore defined; or (c) for compounds of the formula IV wherein $R^7$ is a group $=NOR^8$, reacting a compound of the formula X:

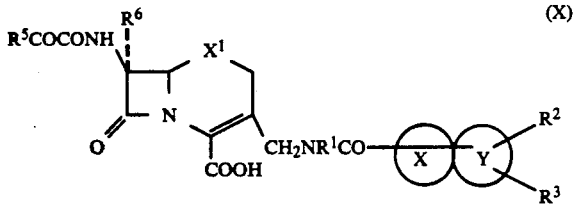

wherein $R^1$, $R^2$, $R^3$, $R^5$, $R^6$, $X^1$, X and Y are as hereinbefore defined, with a compound of the formula: $R^8ONH_2$ wherein $R^8$ is as hereinbefore defined; or (d) for compounds of the formula IV wherein $R^7$ is a group $=NOR^8$ and $R^8$ is other than hydrogen, reacting a compound of the formula IV as hereinbefore defined wherein $R^7$ is a group $=NOH$ with a compound of the formula XI:

$$L^1\text{-}R^{16} \qquad\qquad XI$$

wherein $L^1$ is a leaving group and $R^{16}$ is a group $R^8$ other than hydrogen; or (e) for compounds of the formula IV forming a group $R^5$ by cyclizing an appropriate precursor thereof: wherein any functional groups are optionally protected: and thereafter, if necessary:

(i) removing any protecting group, (ii) for preparing in vivo hydrolysable esters, esterifying corresponding hydroxy groups, (iii) converting compounds wherein $X^1$ is S to compounds wherein $X^1$ is sulphinyl and vice versa, (iv) forming a pharmaceutically acceptable salt.

In the reaction between a cephalosporin compound having a 3-position substituent of the formula: $-CH_2NHR^1$ and a compound of the formula VII, conveniently L is a leaving group such as halo for example chloro, bromo or iodo. Most suitably the reaction is performed under conditions conventional for the reaction of acid halides with amines for example in the presence of an organic amine such as triethylamine. Suitably the reaction is performed at an ambient or lower temperature in a substantially inert solvent such as dimethylformamide and/or dichloromethane. In an alternative aspect the leaving group L is part of an activated ester formed with the acid precursor of the compound of the formula VII, i.e. a compound wherein L is —OH provides an activated ester, e.g. dicyclohexylcarbodi-imide provides an activated ester of the formula VII wherein L is $-OC(NHC_6H_{11})=NC_6H_{11}$, which group is displaced by the cephalosporin having a 3-position substituent of the formula: $-CH_2NHR^1$. Formation and reaction of the active ester is performed in conventional manner in the presence of reaction promotors such as hydroxybenzotriazole and triethylamine, for example in a substantially inert organic solvent such as dimethylformamide at a non-extreme temperature such as 10° C.–50° C.

The cephalosporin starting-materials for this reaction are known from the art, or are made by methods analogous to those of the art. See for example EP-A-127992 and EP-A-164944.

The compounds of the formula VII are either known in the art or are made by methods analogous thereto. For example compounds wherein L is chloro are conveniently prepared from the corresponding acids. The acids are known or are prepared by methods of heterocyclic chemistry known to those skilled in the art, for example as in the hereinafter described Examples.

The reaction between compounds of the formulae VIII and IX is performed under conditions conventional in the cephalosporin art, for example under standard acylation conditions wherein for example the acid is activated as an acid bromide, acid chloride, anhydride or activated ester, or the reaction is performed in the presence of a coupling reagent such as dicyclohexylcarbodi-imide.

The compounds of the formula VIII can be prepared in a manner analogous to that described for the compounds having the 3-substituent of the formula I, with the 7-amino group being optionally protected.

The reaction between compounds of the formula X and $R^8ONH_2$ is performed under conditions standard in the general chemical and/or cephalosporin art. The compounds of the formula X can be prepared in a manner analogous to that described for the compounds having the 3-substituent of the formula I.

The reaction between the compound of the formula IV wherein $R^7$ is a group $=NOH$ and a compound of the formula XI is performed under conditions standard in the general chemical and/or cephalosporin art.

A group $R^5$ may be formed by cyclizing an appropriate precursor. For example compounds of the formulae XII and XIII:

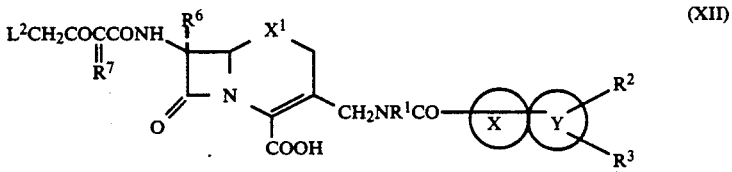

$NH_2CSNH_2$ (XIII)

wherein $R^7$, $R^6$, $X^1$, $R^1$, $R^2$, $R^3$, X and Y are as hereinbeforedefined and $L^2$ is a leaving group, may be reacted to form a 2-aminothiazol-4-yl group. A nitrogen atom of the thiourea may be optionally protected during this cyclization.

The compounds of the formula XII can be prepared in a manner analogous to that described for the compounds of the formula I.

The compounds of the formulae IX, XI and $R^8ONH_2$ are known from, or can be made by the methods of, the general chemical and/or cephalosporin art.

The compounds of the formulae VIII, X and XII are novel and as such form a further aspect of the present invention.

In the process of this invention any functional group can be optionally protected, if appropriate. Such protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxyl protecting group may be the residue of an ester-forming aliphatic or araliphatic alcohol or of an ester-forming phenol, silanol or stannanol (the said alcohol, phenol, silanol or stannanol preferably containing 1-20 carbon atoms).

Examples of carboxyl protecting groups include straight or branched chain (1-12C)alkyl groups (e.g. isopropyl, t-butyl); halo lower alkyl groups (e.g. 2-iodoethyl, 2,2,2-trichloroethyl); lower alkoxy lower alkyl groups (e.g. methoxymethyl, ethoxymethyl, isobutoxymethyl); lower aliphatic acyloxy lower alkyl groups, (e.g. acetoxymethyl, propionyloxymethyl, butyryloxymethyl, pivaloyloxymethyl); lower alkoxycarbonyloxy lower alkyl groups (e.g. 1-methoxy-carbonyloxyethyl, 1-ethoxycarbonyloxyethyl); aryl lower alkyl groups (e.g. p-methoxybenzyl, o-nitrobenzyl, p-nitrobenzyl, benzhydryl and phthalidyl); tri(lower alkyl)silyl groups (e.g. trimethylsilyl and t-butyldimethylsilyl); tri(lower alkyl)silyl lower alkyl groups (e.g. trimethylsilylethyl); and (2-6C)alkenyl groups (e.g. allyl and vinylethyl).

Methods particularly appropriate for the removal of carboxyl protecting groups include for example acid-, base-, metal- or enzymically-catalysed hydrolysis.

Examples of hydroxyl protecting groups include lower alkanoyl groups (e.g. acetyl); lower alkoxycarbonyl groups (e.g. t-butoxycarbonyl); halo lower alkoxycarbonyl groups (e.g. 2-iodoethoxycarbonyl, 2,2,2-trichloroethoxycarbonyl); aryl lower alkoxycarbonyl groups (e.g. benzoyloxycarbonyl, p-methoxybenzyloxycarbonyl, o-nitrobenzyloxycarbonyl, p-nitrobenzyloxycarbonyl); tri lower alkylsilyl (e.g. trimethylsilyl, t-butyldimethylsily) and aryl lower alkyl (e.g. benzyl) groups. In addition two hydroxy groups substituted on adjacent carbon atoms, for example in the catechol moiety, may be protected in the form of a cyclic acetal such as the methylenedioxy moiety.

Examples of amino protecting groups include formyl, aralkyl groups (e.g. benzyl and substituted benzyl, e.g. p-methoxybenzyl, nitrobenzyl and 2,4-dimethoxybenzyl, and triphenylmethyl); di-p-anisylmethyl and furylmethyl groups; acyl (e.g. alkoxycarbonyl and aralkoxycarbonyl e.g. t-butoxycarbonyl and benzyloxycarbonyl); trialkylsilyl (e.g. trimethylsilyl and t-butyldimethylsilyl); alkylidene (e.g. methylidene); benzylidene and substituted benzylidene groups; and the phthalimido group.

The following biological test methods, data and Examples serve to illustrate this invention.

Antibacterial Activity

The pharmaceutically acceptable cephalosporin compounds of the present invention are useful antibacterial agents having a broad spectrum of activity in vitro against standard laboratory microorganisms, both Gram-negative and Gram-position, which are used to screen for activity against pathogenic bacteria. The antibacterial spectrum and potency of a particular compound may be determined in a standard test system. The compounds have particularly high activity in vitro against strains of Pseudomonas aeruginosa.

The antibacterial properties of the compounds of the invention may also be demonstrated in vivo in conventional mouse protection tests.

Cephalosporin derivatives have generally been found to be relatively non-toxic to warm-blooded animals, and this generalisation holds true for the compounds of the present invention. Compounds representative of the present invention were administered to mice at doses in excess of those required to afford protection against bacterial infections, and no overt toxic symptoms or side effects attributable to the administered compounds were noted.

The following results were obtained for representative compounds on a standard in vitro test system using Isosensitest agar medium. The antibacterial activity is described in terms of the minimum inhibitory concentration (MIC) determined by the agar-dilution technique with an inoculum size of $10^4$ CFU/spot.

| | MIC ($\mu$l/ml) EXAMPLE | |
|---|---|---|
| ORGANISM | 1 | 2 |
| P. aeruginosa PU21 (A8101028) | 0.008 | 0.06 |
| Ent. cloacae P99 (A8401054) | 0.015 | 0.03 |
| Serr. marcesens (A8421003) | 0.008 | 0.008 |
| Pr. morganii (A8433001) | 0.008 | 0.008 |
| Kleb. aerogenes (A8391027) | 0.008 | 0.008 |
| E. coli DCO (A8341098) | 0.008 | 0.008 |
| St. aureus 147N (A8601052) | 16 | 2 |
| S. dublin (A8369001) | 0.008 | 0.008 |
| Strep. pyogenes (A681018) | 0.5 | 0.06 |

EXAMPLE 1

7-[2-(2-Aminothiazol-4-yl)-2-((Z)-1-carboxy-1-methylethoxyimino)acetamido]-3-(1-ethyl-1,4-dihydro-4-oxo-1,8-naphthyridine-2-carboxamidomethyl)ceph-3-em-4-carboxylic acid

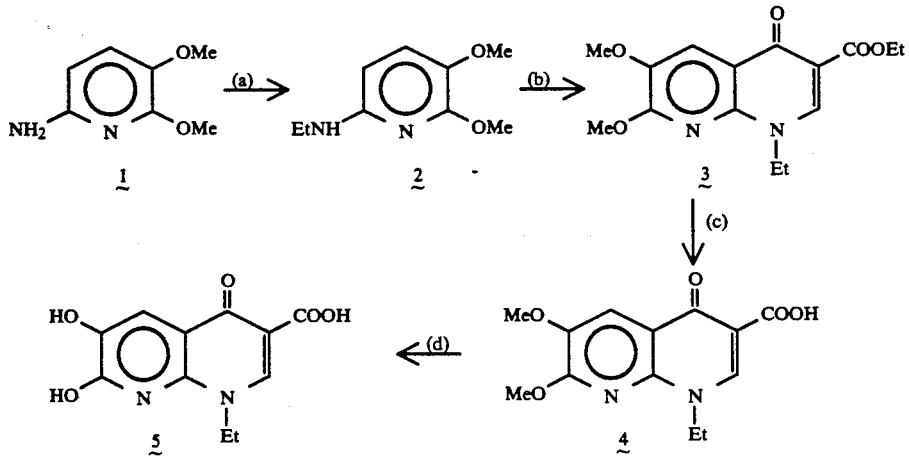

(a) To compound 1 (6 g) (Clark et al., Aust. J. Chem. 1981, 34, 927) in methanol (100 ml), at 0° C., was added sodium cyanoborohydride (2.67 g) and acetaldehyde (2.6 ml) at a pH of 5 maintained with methanolic hydrochloric acid. The solution was stirred for 90 minutes at room temperature and evaporated to give a residue which was dissolved in ether, washed with water and evaporated to give compound 2 (6 g); NMR (CDCl$_3$) 1.45(t,3H); 3.2(dd,2H); 3.75(s,3H); 3.9(s,3H); 5.8(d,1H); 6.95(d,1H).

(b) Compound 2 (6 g) and ethoxymethylene malonate (6.6 ml) were heated at 120° C. for 1 hour. The crude oil was stirred in pentane, evaporated and cyclized with polyphosphoric ester (100 g) at 100° C. for 45 minutes. The mixture was cooled, poured on to ice; the aqueous phase was washed with ether, the pH adjusted to 8 and extracted into ethyl acetate. The solvent was evaporated to give a black solid that was triturated under ether to give compound 3 (3.4 g); NMR (CDCl$_3$) 1.25-1.7 (m,6H); 3.95(s,3H); 4.1(s,3H); 4.2-4.5(m,4H); 8(s,1H); 8.45(s,1H).

(c) Compound 3 (3.3 g) in ethanol (10 ml) and 2N sodium hydroxide (20 ml) was heated under reflux for 90 minutes. Ethanol was evaporated, the aqueous phase acidified to pH2 and the resultant precipitate collected by filtration. Chromatography on silica, eluting with dichloromethane-methanol (98:2) gave compound 4 (1.3 g); NMR (DMSO-d$_6$/CF$_3$COOD) 1.25-1.5(m,3H); 3.9(s,3H); 4.05(s,3H); 4.3-4.7(m,2H); 7.8(s,1H); 8.95(s,1H).

(d) Compound 4 (1.3 g) and boron tribromide (5 ml) were stirred in dichloromethane (10 ml), at room temperature for 3 hours. The solvent was evaporated and the residue hydrolysed by slow addition to ice. The pH was adjusted to 2-3 and the resultant precipitate was collected and purified by chromatography on HP20SS resin (eluting with methanol:water:1% acetic acid (40:60)) (drying by azeotropic distillation using benzene) to give compound 5 (500 mg); NMR (DMSO-d$_6$/CF$_3$COOD/CD$_3$COOD) 1.25-1.5 (m,3H); 4.4-4.7 (m,2H); 7.2(s,1H); 8.85(s,1H).

(e) Compound 5 (250 mg), hexamethyldisilazane (1.26 ml) and saccharin (20 mg) were stirred under reflux in chloroform (10 ml) for 2 hours. The solvent was evaporated under reduced pressure. The residue was dissolved in dichloromethane (5 ml), cooled to −10° C., and triethylamine (1.55 μl) and thionyl chloride (80 μl) were added. The mixture was stirred for 30 minutes at room temperature and then added to 3-aminomethyl-7-[2-(2-aminothiazol-4-yl)-2-((Z)-1-carboxy-1-methylethoxyimino)acetamido]ceph-3-em-4-carboxylic acid (484 mg) in dimethylformamide (5 ml) in the presence of triethylamine (700 μl), at 0° C., for 15 minutes. The solvent was evaporated and the residue purified over HP20 resin (eluting with methanol-water-1% acetic acid (70:30) to give the product cephalosporin (130 mg); NMR (DMSO-d$_6$/CF$_3$COOD/CD$_3$COOD) 1.25-1.5(m,3H); 1.5(s,6H); 3.5-3.7(m,2H); 3.9-4.6(m,4H); 5.15(d,1H); 5.8(d,1H); 7, 7.65 and 8.6 (3s,3H).

EXAMPLE 2

7-[2-(2-Aminothiazol-4-yl)-2-((Z)-ethoxyimino)acetamido]-3-(1-ethyl-1,4-dihydro-4-oxo-1,8-naphthyridine-2-carboxamidomethyl)ceph-3-em-4-carboxylic acid To compound 5 (from Example 1) (160 mg) was added trimethylsilyl chloride (480 μl) and triethylamine (630 μl) in chloroform (10 ml). The mixture was stirred under reflux for 90 minutes, cooled to 0° C. and thionyl chloride (102 μl) and triethylamine (196 μl) were added. The mixture was stirred at room temperature for 30 minutes, evaporated and added to a solution of 3-aminomethyl-7-[2-(2-aminothiazol-4-yl)-2-((Z)-ethoxyimino)acetamido]ceph-3-em-4-carboxylic acid (270 mg) in dimethylformamide (10 ml) in the presence of triethylamine (440 μl). This mixture was stirred at 0° C. for 15 minutes, evaporated and purified over HP20 resin (eluting with methanol:1% acetic acid (70:30)) to give the product cephalosporin (100 mg); NMR (DMSO-d$_6$/CF$_3$COOD/CD$_3$COOD) 1.25-1.5(m,6H); 3.2-3.8(m,2H); 4.0-4.7(m,6H); 5.15(d,1H); 5.75(d,1H); 7.0(s,1H); 7.65(s,1H); 8.7(s,1H).

EXAMPLE 3

7-[2-(2-Aminothiazol-4yl)-2-((Z)-1-carboxy-1-methylethoxyimino)acetamido-3-(3,4-dihydroxyquinoline-5-carboxamidomethyl)ceph-3-em-4-carboxylic acid To a solution of 3,4-dihydroxyquinoline-5-carboxylic acid (51 mg) in chloroform (5 ml) and triethylamine (0.207 ml) was added trimethylsilyl chloride (0.19 ml). The mixture was heated at 55°-60° C. for 5 hours, cooled and treated, successively, with triethylamine (0.038 ml) and thionyl chloride (0.020 ml). After 30 minutes the mixture was added to 3-aminomethyl-7-[2-(2-aminothiazol-4-yl)-2-((Z)-1-carboxy-1-methylethoxyimino)acetamido]ceph-3-em-4-carboxylic acid (120 mg) in methanol (10 ml) containing triethylamine (0.14 ml) at 0° C. The mixture was stirred for 1 hour at 0° C., diluted with water, acidified to pH2 and concentrated under reduced pressure. The residue was subjected to chromatography on HP20SS resin to give the title compound (27 mg); NMR (DMSO-$d_6$/CD$_3$COOD/CF$_3$COOD) 1.55(s,6H); 3.70(m,2H); 4.40(m,2H); 5.25(d,1H); 5.85(d,1H); 7.10(s,1H); 7.55(d,1H); 7.80(t,1H); 8.0(d,1H); 8.5(s,1H).

The quinoline carboxylic acid was obtained as follows:

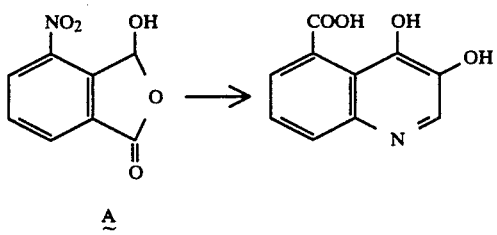

Compound A (2.5 g) in ethanol (50 ml) was hydrogenated, for 90 minutes, at atmospheric pressure over 10% palladium on charcoal (250 mg). The mixture was filtered and concentrated to about 10 ml by heating at 40° C. under reduced pressure.

In another flask, potassium cyanide (1.5 g) was added to 1M sodium carbonate solution (50ml). Nitrogen was bubbled through the solution for 30 minutes, glyoxal bisulphite (4.15 g) added and the product of the hydrogenation described above. The mixture was stirred for 2.5 hours, acidified to pH2 with 6N HCl and the resultant solid was collected by filtration, washed and dried to give 3,4-dihydroxyquinoline-5-carboxylic acid (770 mg); MS (EI): 205(M+·), 187 (M-H$_2$O+·, 161 (M-CO$_2$)+·.

EXAMPLE 4

7-[2-(2-Aminothiazol-4-yl)-2-((Z)-1-carboxy-1-methylethoxyimino)acetamido]-3-(2,3-dihydroxyquinoline-4-carboxamidomethyl)ceph-3-em-4-carboxylic acid Trimethylsilylchloride (191 μl, 1.5 mM) was added to a stirred suspension of 4-carboxy-3-hydroxyquinol-2-one (51 mg, 0.25 mM) in chloroform (2 ml) under an atmosphere of argon, triethylamine was then added 208 μl, 1.5 mM) and the mixture left to stir for 30 minutes. Thionyl chloride (20 μl, 0.275 mM), triethylamine (38 μl, 0.275 mm) and dimethylformamide (2-4 μl:catalytic amount) were added in succession and the reaction mixture left to stir for 1.5 hours. This solution was then added quickly via a syringe to a cooled (ice/water bath) solution of silylated 3-aminomethyl-7-[2-(2-aminothiazol-4yl)-2-((Z)-1-carboxy-1-methylethoxyimino)acetamido]ceph-3-em-4-carboxylic acid under an atmosphere of argon, left to stir for 15 minutes at 0° C. and then for 90 minutes at room temperature. Solvent was removed by evaporation and the residue was triturated with water (10 ml) and the precipitate collected by filtration to give the crude product (280 mg), which was purified by HPLC on silica (C18) eluting with acetonitrile/water/trifluoroacetic acid (22.5/77.5/0.1) to give the title compound (70 mg); NMR (DMSO$d_6$/CF$_3$COOD) 1.49(s,3H); 1.51(s,3H); 3.54(d,1H); 3.72(d,1H); 4.17 and 4.23(dd,1H); 4.50 and 4.58(dd,1H); 5.19(d,1H); 5.86 and 5.84(dd,1H); 7.06(s,1H); 7.09-7.2(m,1H); 7.2-7.4(m,3H); 8.79(t,1H); 9.70(d,1H).

EXAMPLE 5

7-[2-(2-Aminothiazol-4-yl)-2-((Z)-1-carboxy-1-methylethoxyimino)acetamido]-3-(2,3-dihydroxyquinoline-8-carboxamidomethyl)ceph-3-em-4-carboxylic acid To a solution of 3-hydroxy-8-carboxy-2(1H)-quinolinone (160 mg) in chloroform (15 ml) was added triethylamine (0.62 ml) and speedily trimethylsilyl chloride (0.57 ml). The mixture was heated to 60° C. for 4 hours, cooled to 0° C. and treated with triethylamine (0.114 ml) and thionyl chloride (0.06 ml), whereupon the resultant solution was stirred for 2 hours at 0° C. and at room temperature for 30 minutes. This solution was added to 3-aminomethyl-7-[2-(2-aminothiazol-4-yl)-2-((Z)-1-carboxy-1-methylethoxyimino)acetamido]ceph-3-em-4-carboxylic acid (360 mg) in methanol (30 ml) containing triethylamine (0.42 ml) at 0° C. The reaction mixture was stirred for 30 minutes at 0° C., stirred for 30 minutes at room temperature, diluted with water, acidified to pH2, concentrated, and purified by chromatography (HP20SS resin eluting with methanol/water/acetic acid) to give the title compound (85 mg); NMR (DMSO-$d_6$/CD$_3$COOD/CF$_3$COOD) 1.50(s,6H); 3.55(m,2H); 4.40(m,2H); 5.1(d,1H); 5.75(d,1H); 7.00-7.25(,3H); 7.6(d,1H); 7.80(d,1H).

The starting material was obtained as follows:

A suspension of 7-methoxycarbonylisatin (2.4 g) in ether (50 ml) was treated at 31 5° C. with a solution of diazomethane (1.5 g) in ether (140 ml). The mixture was stirred for 3 hours and acetic acid (3 ml) added. The mixture was filtered and the filtrate concentrated under reduced pressure to give a residue that was purified by column chromatograph (silica gel eluting with dichloromethane/methanol) to give 3-hydroxy-8-methoxycarboxy-2-(1H)-quinolinone (350 mg). This in methanol (10 ml) was treated with 2N sodium hydroxide (1.75 ml) at room temperature for 2.5 hours. The mixture was acidified with 2N HCl and the precipitate was collected and dried to give 3-hydroxy-8-carboxy-2(1H)-quinolinone (180 mg); NMR (DMSO-$d_6$/CF$_3$COOD) 7.12-7.30(m,2H); 7.75(d,1H); 8.01(d,1H).

We claim:
1. A compound of formula (IV)

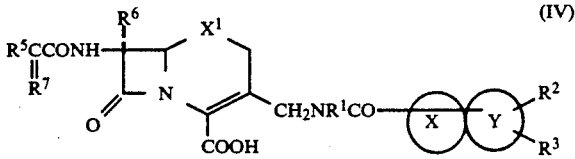

or a salt or ester thereof;
wherein:
$X^1$ is sulphur or sulphinyl;
$R^1$ is hydrogen, $C_{1-6}$alkyl optionally substituted by halo, hydroxy, $C_{1-4}$alkoxy, carboxy, amino, cyano, $C_{1-6}$alkanoylamino, phenyl or heteroaryl, or $R^1$ is $C_{2-6}$alkenyl;
$R^2$ is hydroxy or an in vivo hydrolyzable ester thereof;

$R^3$ is ortho to $R^2$ and is hydroxy or an in vivo hydrolyzable ester thereof;

X is a ring selected from a group of the sub-formulae (a)-(b):

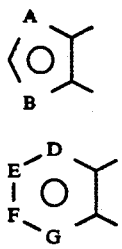

wherein A is CH or a nitrogen atom; B is oxygen, sulphur or a group $NR^4$; zero, one or two of D, E, F and G are nitrogen atoms and the remainder are CH groups; or X is a pyrazinone, pyridinone, pyridazinone or pyrimidinone ring, or is a thione equivalent of such a ring, said rings having a substituent $R^4$ on one nitrogen atom, or is pyranone, or pyranthione; the ring X being fused by any two adjacent carbon atoms to ring Y;

$R^4$ is hydrogen, hydroxy, $C_{1-6}$alkoxy, phenoxy, $C_{2-6}$alkenyl or $C_{1-6}$alkyl, (any of these groups being optionally substituted by hydroxy, $C_{1-6}$alkoxy, cyano, amino, $C_{1-6}$alkylamino, di-$C_{1-6}$alkylamino, carboxy, $C_{1-6}$alkoxycarbonyl, $C_{1-6}$alkanoyloxy, carbamoyl, $C_{1-6}$alkylcarbamoyl, di-$C_{1-6}$alkylcarbamoyl, $C_{1-6}$alkoxycarbonylamino, phenyl phenyl$C_{1-6}$alkyl, carboxyaminocarbonyl, $C_{1-6}$alkoxycarbonylaminocarbonyl, benzoyl or $C_{3-6}$cycloalkyl) or $R^4$ is phenyl, $C_{3-6}$ cycloslkyl, amino, $C_{1-8}$alkamino or di-$C_{1-6}$alkylamino:

wherein the fused X-Y ring system and/or any phenyl group is further optionally substituted by $C_{1-6}$alkyl, halo, hydroxy, hydroxy, $C_{1-6}$alkyl, cyano, trifluoromethyl, nitro, amino, $C_{1-6}$alkylamino, di-$C_{1-6}$alkylamino, $C_{1-6}$alkanoyl, $C_{1-6}$alkoxy, $C_{1-6}$alkylthio, $C_{1-6}$ alkanoyloxy, carbamoyl, $C_{1-6}$alkylcarbamoyl, di-$C_{1-6}$ alkyl carbamoyl, carboxy, carboxy $C_{1-6}$ alkyl, $C_{1-6}$alkoxycarbonyl $C_{1-6}$alkyl, sulpho sulpho-$C_{1-6}$alkyl, sulphonamido $C_{1-6}$alkyl, $C_{1-6}$alkoxycarbonyl, $C_{1-6}$alkanoylamino, thioureido or amidino;

ring Y is a 6-membered heteroaryl ring containing only ring atoms selected from carbon and one or two nitrogen atoms, substituted on adjacent carbon atoms by groups $R^2$ and $R^3$;

wherein either ring of the fused X-Y ring system is bonded via a carbon atom to the amide linkage;

$R^5$ is a 2-aminothiazol-4-yl or 2-aminooxazol-4-yl each optionally substituted in the 5-position by fluorine, chlorine or bromine, or $R^5$ is 5-aminoisothiazol-3-yl, 5-amino-1,2,4-thiadiazol-3-yl, 3-aminopyrazol-5-yl, 3-aminopyrazol-4-yl, 2-aminopyrimidin-5-yl, 2-aminopyrid-6-yl, 4-aminopyrimidin-2-yl, 2-amino-1,3,4-thiadiazol-5-yl or 5-amino-1-methyl-1,2,4-triazol-3-yl;

$R^6$ is hydrogen, methoxy or formamido; and $R^7$ is of the formula $=N.O.R^8$ (having the syn configuration about the double bond) wherein $R^8$ is hydrogen, (1-6C)alkyl, (3-8C)cycloalkyl, (1-3C)alkyl(3-6C) cycloalkyl, (3-6C)cycloalkyl(1-3C)alkyl, (3-6C)alkenyl, optionally substituted by carboxy, (5-8C)cycloalkenyl, (3-6C)alkynyl, (2-5C)alkylcarbamoyl, phenylcarbamoyl, benzylcarbamoyl, (1-4C)alkylcarbamoyl(1-4C)alkyl, di(1-4C)alkylcarbamoyl(1-4C)alkyl, (1-4C)haloalkylcarbamoyl(1-4)alkyl, (1-3C)haloalkyl, (2-6C)hydroxyalkyl, (1-4C)alkoxy(2-4C)alkyl, (1-4C)alkylthio(2-4C)alkyl, (1-4C)alkenesulphinyl(1-4C)alkyl, (1-4C)alkanesulphonyl(1-4C)alkyl, (2-6C)aminoalkyl, (1-4C)alkylamino(1-6C)alkyl, (2-8C)dialkylamino(2-6C)alkyl, (1-5C)cyanoalkyl, 3-amino-3-carboxypropyl, 2-(amidinothio)ethyl, 2-(N-aminoamidinothio)ethyl, tetrahydropyran-2-yl, thietan-3-yl, 2-oxopyrrolidinyl, or 2-oxotetrahydrofuranyl, or $R^8$ is of the formula V:

$$—(CH_2)_q—C(COOH)=CR^9R^{10} \qquad V$$

wherein q is one or two and $R^9$ and $R^{10}$ are independently hydrogen or $C_{1-4}$alkyl; or $R^8$ is of the formula VI:

$$—CR^{11}R^{12}—(CH_2)_r—COR^{13} \qquad VI$$

wherein r is 0-3, $R^{11}$ is hydrogen, (1-3C)alkyl or methylthio, $R^{12}$ is hydrogen, (1-3C)alkyl, (3-7C) cycloalkyl, cyano, carboxy, (2-5C)carboxyalkyl or methanesulphonylamino, or $R^{11}$ and $R^{12}$ are joined to form, together with the carbon to which they are attached, a (3-7C)carbocyclic ring, and $R^{13}$ is hydroxy, amino, (1-4C)alkoxy, (1-4C)alkylamino or of the formula $NHOR^{14}$ in which $R^{14}$ is hydrogen or (1-4C)alkyl;

or $R^7$ may be of the formula $=CH.R^{15}$ wherein $R^{15}$ is hydrogen, halogen, (1-6C)alkyl, (3-7C)cycloalkyl, (2-6C)alkenyl, (3-7C)cycloalkenyl, phenyl or benzyl.

2. A method of treating a bacterial infection in a mammal comprising administering to the mammal an amount of the compound according to claim 1 sufficient to effect the treatment.

3. A compound according to claim 1 wherein $R^2$ and $R^3$ are both hydroxy.

4. A compound according to claim 1 wherein the cephalosporin compound has a 3-position substituent of the formula (II):

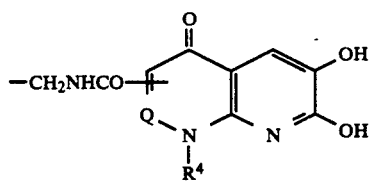

wherein Q is CH or N and $R^4$ is hydrogen, $C_{1-6}$alkyl or $C_{1-6}$alkoxy.

5. A compound according to claim 1 wherein the cephalosporin compound has a 3-position substituent of the formula (III):

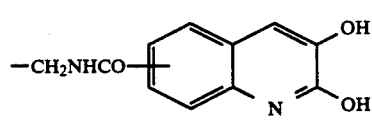

6. A compound according to claim 1 wherein $R^8$ is 2-carboxyprop-2-yl.

7. A compound according to claim 1 which is:

7-[2-(2-Aminothiazol-4-yl)-2-((Z)-1-carboxy-1-methylethoxyimino)acetamido]-3-(1-ethyl-1,4-dihydro-4-oxo-1,8-naphthyridine-2-carboxamidomethyl)ceph-3-em-4-carboxylic acid, 7-[2-(2-Aminothiazol-4-yl)-2-((Z)-ethoxyimino)acetamido]-3-(1-ethyl-1,4-dihydro-4-oxo-1,8-naphthyridine-2-carboxamidomethyl)ceph-3-em-4-carboxylic acid, 7-[2-(2-Aminothiazol-4-yl)-2-((Z)-1-carboxy-1-methylethoxyimino) acetamido-2-(3,4-dihydroxyquinoline-5-carboxamidomethyl)ceph-3-em-4-carboxylic acid, 7-[2-(2-Aminothiazol-4-yl)-2-((Z)-1-carboxy-1-methylethoxyimino)acetamido]-3-(2,3-dihydroxyquinoline-4-carboxamidomethyl)ceph-3-em-4-carboxylic acid, or (7-[2-(2-Aminothiazol-4-yl)-2-((Z)-1-carboxy-1-methylethoxyimino)acetamido]-3-(2,3-dihydroxyquinoline-8-carboxamidomethyl)ceph-3-em-4-carboxylic acid.

8. An antibacterial composition comprising an antibacterially effective amount of a compound according to claim 1 and a pharmaceutically acceptable carrier.

* * * * *

UNITED STATES PATENT AND TRADEMARK OFFICE
CERTIFICATE OF CORRECTION

PATENT NO. : 5,008,259
DATED : April 16, 1991
INVENTOR(S) : Siret et al

It is certified that error appears in the above-identified patent and that said Letters Patent is hereby corrected as shown below:

On the title page, Item [30] to read as follows:

--[30]   Foreign Application Priority Data
May 10, 1988 [EPA]   European Patent...88401143.8--

Signed and Sealed this

Twenty-second Day of September, 1992

Attest:

DOUGLAS B. COMER

*Attesting Officer*   Acting Commissioner of Patents and Trademarks